United States Patent [19]
Buckley

[11] Patent Number: 5,003,971
[45] Date of Patent: Apr. 2, 1991

[54] EXPANSION SYSTEM FOR A MEDICAL AND SURGICAL DRESSING

[76] Inventor: John T. Buckley, 175 Sasco Hill Rd., Fairfield, Conn. 06430

[21] Appl. No.: 239,701

[22] Filed: Sep. 2, 1988

[51] Int. Cl.$^5$ ............................................... A61L 15/00
[52] U.S. Cl. ..................................... 128/156; 128/155
[58] Field of Search ............... 128/155, 156, 888, 889, 128/890, 891, 892, 893, 894, 163, 167, 168, 169, 170, 171, 335

[56] References Cited
U.S. PATENT DOCUMENTS

3,976,066 8/1976 McCartney ........................ 128/889
4,846,820 7/1989 Jensen .................................. 604/339

Primary Examiner—Alan W. Cannon
Assistant Examiner—N. Paul
Attorney, Agent, or Firm—Eric Y. Munson; Mark P. Stone

[57] ABSTRACT

A medical and surgical dressing has an expansion system designed to cover, yet be spaced apart from, a healing wound when the dressing is applied. In its expanded configuration, the dressing is bubble shaped. The dressing includes an adhesive material for adhering to the skin of a patient surrounding the wound, and further includes several layers of material which permit circulation and filtration of air entering the space defined by the expanded bubble. The dressing and expansion system avoid direct contact with the healing wound, yet fully protect the wound from the outside environment.

28 Claims, 7 Drawing Sheets

EXPANSION SYSTEM FOR A MEDICAL AND SURGICAL DRESSING

DISCUSSION OF THE BACKGROUND ART

Wounds and damage to several skin levels of mammals are of many different types. Burns, chemically induced damage, cuts and slashes, openings to the flesh from surgery, shredding of flesh, wounds oozing pus and other substances, require conditions as aseptic as possible. Circulation of air free of harmful bacteria, and non-contact of the heal area with any other material (including the medical dressing) is desired in numerous instances. Medical dressings should be capable of easy and safe removal to enable inspection of the heal area and application of a clean dressing without damaging the heal area. Such damage can occur during removal of conventional dressings (including, in may instances, dressing having so called "non-stick" characteristics) by tearing or injuring the healing tissue by friction and abrasion, or by adherence of part or all the healing tissue to the dressing being removed.

Medical dressings should also protect the heal area from further damage which might result from contact with external objects, such as accidental impact of the heal area against an object, the force of which is transmitted through the medical dressing and aggravates the damage to the wound, in some cases opening the heal area which has begun to close and heal. When the patient is sleeping, accidental contact with other objects may damage the heal area when conventional dressings are used. Patients such as young children or pet animals may attempt to scrape the medical dressing against other objects, either to relieve itching, or because of their aversion to having the medical dressing attached to their body. If the medical dressing rests directly on the heal area, such action by the patient can aggravate the damage of the heal area. The dressing should permit application of liquids or ointments to the heal area to assist the healing process, yet not come into contact with such medicines nor absorb them. Medical dressings ideally should serve all these healing and protective functions. In some situations, the pressure of a conventional bandage can help clotting of small bleeding wounds not requiring sutures. However, when bleeding from such minor wound has ceased, the conventional dressings are subject to the disadvantages discussed above, namely that they interfere with the wound and healing process.

Conventional medical dressings often have a gauze layer which attempts to fulfill a dual function of permitting air to flow to and from the heal area and to absorb liquid type materials from the wound. However, once the gauze has absorbed liquid materials such as blood which soon congeals and hardens, the gauze obviously ceases to serve the function of permitting air to flow to and from the heal area. Moreover, the gauze may adhere directly to the wound.

Additionally, medical dressings should be easy to apply even by persons untrained in medicine, and be easy to form into desired shapes to house the heal area and free the heal area from contact with the medical dressing.

Further, medical dressings ideally should be capable of mass production at moderate costs and convenient packaging and storage if they are to fulfill the goal of widespread use by non-medical persons to better protect heal areas not requiring medical attention but which are not adequately protected by existing mass produced non-prescription medical dressings.

Also, medical dressings should be of sufficient sophistication that persons trained in medicine have great flexibility in shaping the dressings in a manner that best serves the patient's needs.

It is an object of the present invention to provide an improved medical dressing overcoming the disadvantages of the known dressings described above.

SUMMARY OF THE INVENTION

The present invention provides a medical or surgical dressing including an expansion system enabling the protective portion of the dressing to be spaced apart from a wound area when the adhesive portion of the dressing is affixed to the skin of the patient. In the preferred embodiment, the dressing includes a plurality of layers, at least one of which permits circulation and filtration of air between the space defined by the expanded dressing and the ambient environment external to the dressing. Another dressing layer is formed from criss-crossed fibers adapted to engage locking means for the expansion system when the dressing is spaced apart from the wound in its expanded configuration.

In the preferred embodiment of the invention, the expansion system is provided immediately adjacent to the dressing layer including the criss-crossed fibers. The expansion system includes a plurality of hooks adapted to engage both the hub or center portion of the layer of criss-crossed fiber and the peripheral end of that adjacent layer. The hooks engaging the peripheral portions of the dressing are selectively exposed by movement of a protective cylinder when it is desired to place the dressing in its expanded operative position. Alternative support and locking arrangements for the expansion system for the dressing are also described.

The dressing of the present invention may be packaged flat, in a manner similar to conventional dressings, and stored in a flat position until expansion is desired. In its operative position, the dressing advantageously provides protection for a wound area without contact with the wound itself to enhance and promote the healing process. Healing is further enhanced by employing dressing layers which permit circulation of fresh air into and out of the expanded space defined by the dressing over the wound area, and also provide means for filtering the incoming air to remove dust and other harmful foreign materials therefrom. The expansion system of the dressing of the present invention also advantageously enables the person applying the dressing to adjust the size and/or overall configuration of the space surrounding the wound, to a limited degree, so that the dressing may be shaped in a manner that best serves an individual patient's needs.

It is further within the scope of the invention to provide a dressing comprising a single layer of material having memory so that it may be readily, selectively, and non-permanently transformed into many different expanded operative configurations as may be desired. Preferably, the single layer will be air permeable to permit circulation of air into the wound area and filter any undesireable matter carried by the air.

It is further within the scope of the invention to provide a dressing in a preformed and permanently expanded configuration. In a manner similar to that discussed above, the material forming the permanently expanded configuration of the dressing preferably will permit circulation and filtration of air entering the wound area.

BEST MODE FOR CARRYING OUT THE INVENTION

Figure 1:
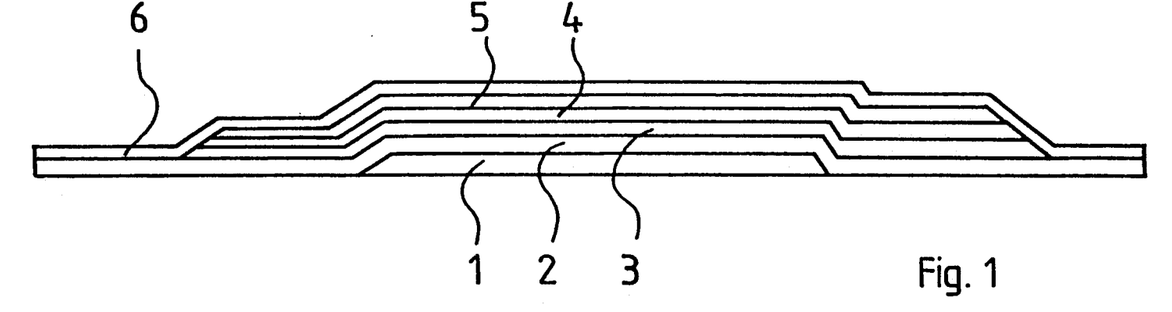
FIG. 1 of the drawings illustrates a side elevational view of the expandable medical dressing in accordance with the present invention in its non-expanded flat storage configuration.

Referring first to FIG. 1 of the drawings, this figure illustrates a side elevational view of the medical dressing in accordance with the present invention, before it has been extended into an expandable operative position. The medical dressing is generally designated by the reference numeral 1. As illustrated by FIG. 1, the dressing includes six adjacent layers successively mounted atop one another stacked in a direction between the inner dressing surface (layer No. 1) through the outer dressing surface (layer No. 6). The inner layer No. 1, in its operative position, is adjacent to a wound, while the outer layer No. 6 defines the outer surface of the dressing. Each of the layers (1-6) are formed from an expandable or elastic material which is also air permeable. The outer surface of each individual layer adheres to the inner surface of the next successive adjacent layer, so that the assembled dressing defines a single mass formed from the combined individual layers.

Layer No. 1 of the dressing, which is closest to a wound area of the patient to be treated, is formed by a material which does not easily adhere to the wound area, even if Layer No. 1 inadvertently comes into contact with blood or other substances in the wound area. However, Layer No. 1 does permit air to permeate through it, together with any liquid from the wound area. Liquid material flowing through Layer No. 1 will be absorbed by the next successive adjacent Layer No. 2. Layer No. 1 is optional since the dressing, in its operative expanded position, is not intended to come into contact with the wound area. However, Layer No. 1 is employed as an added precaution in the event that such contact should inadvertently occur.

The next outer layer No. 2 is formed form an absorbent aseptic material, generally a gauze, which permits ambient air to flow between the wound area covered by the dressing and the ambient environment external to the dressing. Layer No. 2 defines small openings of sufficient size to filter out dust, other undesired foreign objects, and certain bacteria. The size of the openings or pores may be varied.

The next successive adjacent outer layer No. 3 is formed from a material having a plurality of criss-crossed rough fibers. As will be explained below, the function of Layer No. 3 is to engage and hold small hooks or other locking means forming part of the expansion and support structure for the dressing when the dressing is extended into an expanded configuration.

The next adjacent successive outer layer No. 4 comprises the support and expansion system of the present invention, as will be discussed below. Layer No. 5 is formed from a material identical of that of layer No. 3, and serves to enhance the effectiveness of the anchoring capability of layer No. 3 as it cooperates with the support and expansion system of layer No. 4. As will be discussed in more detail below, both layers No. 3 and 5, which surround the support and expansion system of layer No. 4, are adapted to engage locking means of the suport and expansion system to provide structural support for the dressing in its expanded, operative configuration.

The outermost layer No. 6 provides the outer surface and protective covering for the overall dressing 1. The remote ends or periphery of layer No. 6 include an adhesive material applied to the inner surface of the layer. In this manner, the inner surface of layer No. 6 is applied to the skin of a patient at an area which is substantially remote from the wound heal area. The outer surface of layer No. 6 may be coated with a protective (wear resistant) yet air permeable material to protect both the wound area and the inner layers disposed beneath the outer layer No. 6, yet permit air flow into and out of the wound area. As illustrated by FIG. 1, the remote ends or periphery of outer layer No. 6 extend beyond the periphery of the inner layers therebelow, to assure that the portions of outer layer No. 6 adapted to adhere to the skin of a patient do so only at locations remote from the wound area.

Figure 2:
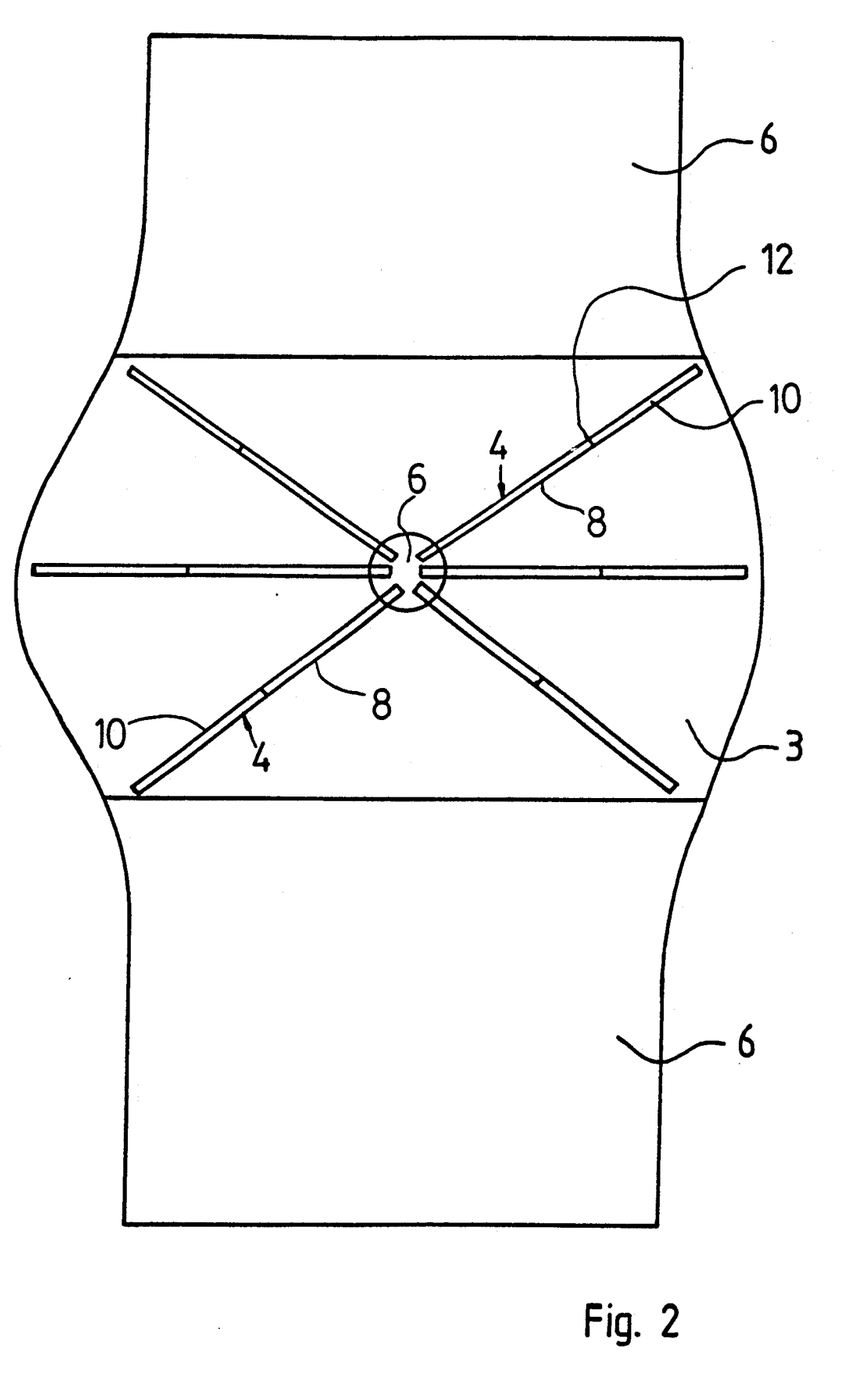
FIG. 2 is a top plan view of the dressing in FIG. 1, partly in section, illustrating layer number 3 and the expansion support system mounted thereatop.
Figure 3A:
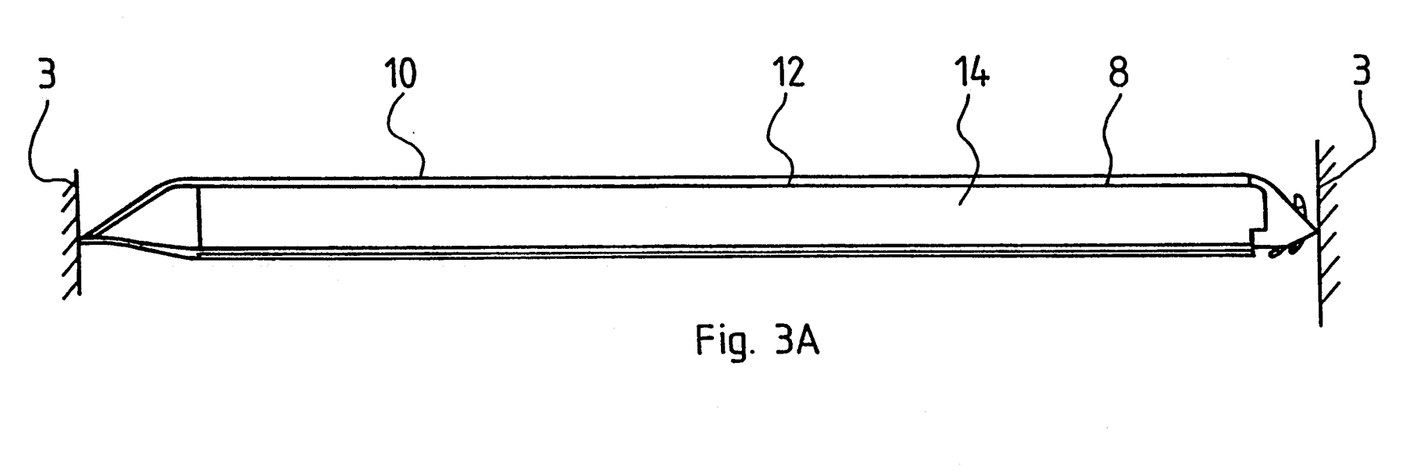
FIGS. 3A, 3B, 3C, and 3D illustrate details of the support and expansion system generally shown by FIG. 2.
Figure 3B:
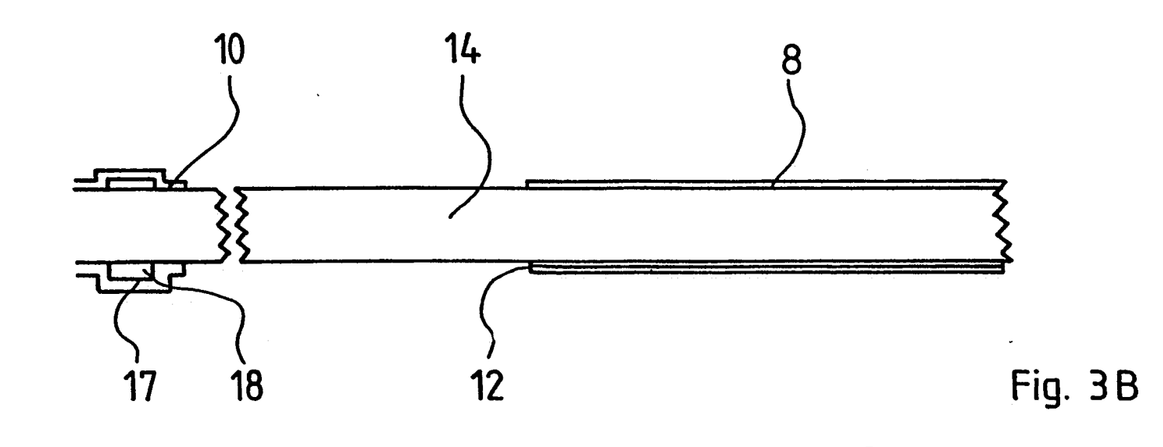
Figure 3C:
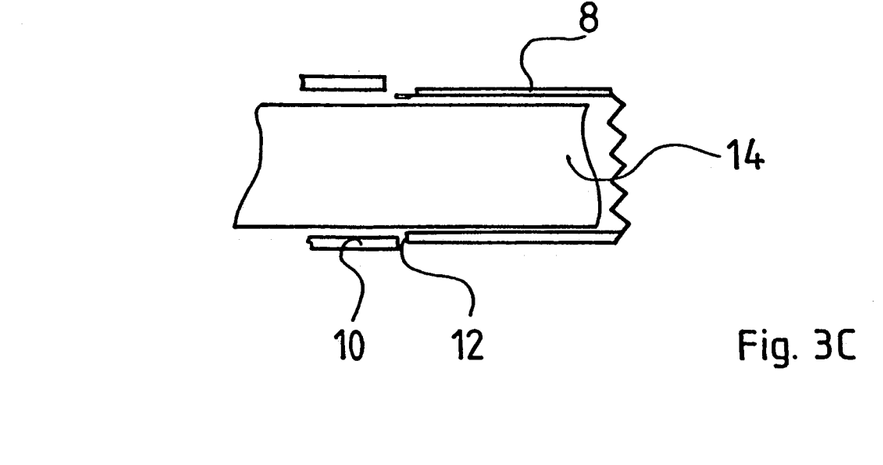
Figure 3D:
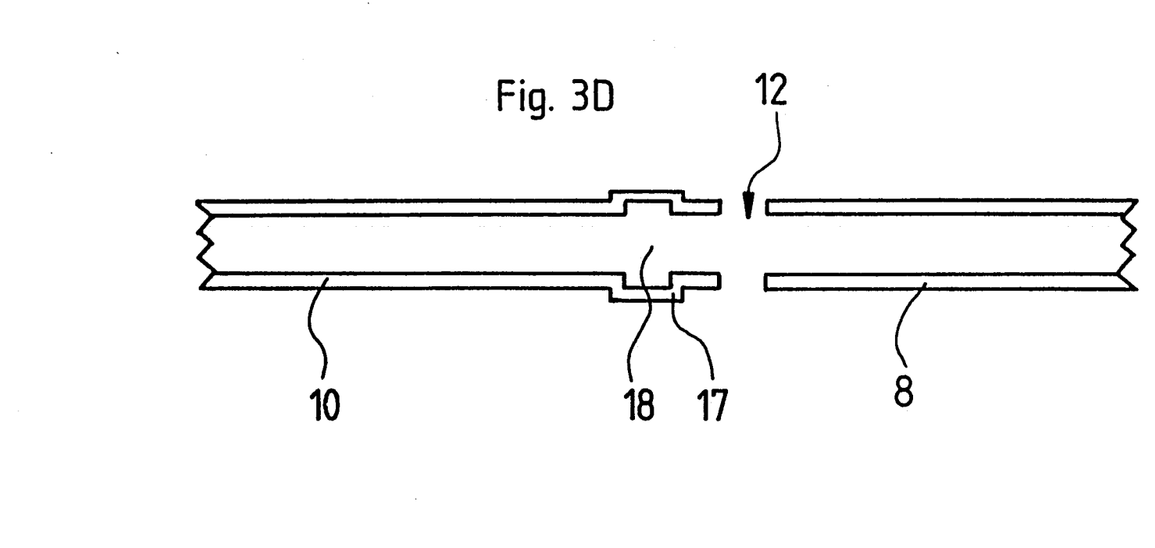

FIG. 2 of the drawing illustrates a top plan view of the dressing of FIG. 1, in which both layer No. 3 and the support and expansion system of layer No. 4 are exposed. The support and expansion system includes a plurality of tubes or hollow cylinders 4 arranged in a radial or spoke-like configuration extending from a hub area 6 centrally defined on layer No. 3 to the outer periphery of layer No. 3. As more fully illustrated by FIGS. 3A-D, each tube 4 is defined by an inner hub tube 8 and an outer peripheral tube 10. In the non-expanded configuration of the dressing as shown in FIG. 2, the adjacent ends of tubes 8 and 10 abut against each other at the position designated by reference no. 12 of FIG. 2. As illustrated more clearly in FIGS. 3A, 3B, and 4, a cylinder or rod 14 is received within both the hub and perimeter tubes 8 and 10. The end of the hub tube is anchored to layer No. 3 at its inner end adjacent to the center hub region of that layer. In a similar manner, the remote or the distant end of the perimeter tube is anchored to layer No. 3. As discussed above, layer No. 3 comprises criss-crossed fibers and the anchoring of the hub and perimeter tubes may be accomplished by providing hooks on the ends of the respective tubes for engaging the criss-crossed fibers of layer No. 3. The hub and perimeter tubes are selectively movable apart from one another for exposing portions of the outer surface of the cylinder 14 received within the tubes. Preferably, the tubes 8 and 10 and the cylinder 14 are formed from plastic to facilitate relative movement and sliding between the respective tubes and the cylinder 14. A locking chamber 18, defined by a flange 17 in the perimeter tube 10, is illustrated by FIGS. 3B and 3D.

Figure 4:
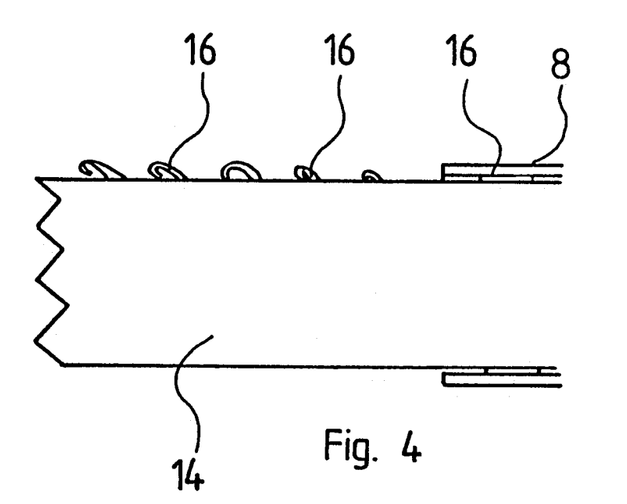
FIG. 4 of the drawing illustrates the details of one embodiment of the locking means for the expansion and support system of the present invention.

Referring now to FIG. 4 of the drawings, the cylinder 14 is shown in detail. A plurality of hooks 16 are carried on the outer surface of the cylinder 14. FIG. 4 illustrates the relationship between the cylinder 14 and the hub tube 8 after the perimeter tube 10 has been moved away from the hub tube 8 in the expanded configuration of the dressing. When the perimeter tube 10 is separated from the hub tube 8, a portion of the outer surface of the cylinder 14 is exposed, thereby exposing the hooks 16 carried thereby. The hooks 16 carried by the unexposed portion of cylinder 14 still remain shielded by the hub tube 8 as shown in FIG. 4, or, in a similar manner, by the perimeter tube 10 (not shown in FIG. 4). As will be described more fully below, the hooks 16 are adapted to engage the criss-crossed fibers of the surrounding dressing layers No. 3 or 5 to maintain and support the dressing in an expanded configuration.

As discussed, when the hub and perimeter tube are moved apart from each other, hooks 16 and at least a portion of the cylinder 14 are exposed. These hooks are adapted to engage the criss-crossed fibers of the dressing layer No. 3 and/or layer No. 4 proximate to the periphery of these anchoring layers. If the engagement is secure, the dressing structure will be maintained in an expanded configuration. However, to provide additional support, a deformable or resilient member such as an expansion spring may be positioned within the locking chamber 18 defined by the flange portion 17 of the perimeter tube 10. The spring will be compressed as long as the cylinder 14 is still received within the end of the perimeter tube 10 defining the flange 17. However, once the cylinder is removed from position 18, the spring expands to a size greater than the sectional area of the cylinder 14, thereby preventing any retraction of the cylinder 14 back into the end space 18 of the perimeter tube.

In operation of the invention when the medical dressing of FIG. 1 is to be applied to protect a wound, the person applying the dressing presses or otherwise exerts an outwardly directed force on the central area of the inner surface of layer No. 1 of the dressing when the dressing is in its flat storage configuration, as illustrated by FIG. 1. The outwardly directed pressure is transmitted to layer No. 4 comprising the support and expansion system, and forces the perimeter and hub tubes to separate from one another. As discussed, the separation of the hub and perimeter tubes exposes a portion of the cylinder 14 received therein, thereby exposing the hooks 16 carried on the exposed cylinder surface. The deformation of the elastic layers of the dressing, and in particular layer No. 3 beneath the expansion and support system, into a concave or bubble shaped configuration causes the exposed hooks 16 of the cylinder 14 to engage the criss-crossed fibers of layer No. 3 of the dressing towards the outer surface or periphery of the now expanded layer No. 3. After the hooks have so engaged layer No. 3, pressure applied to the dressing by the applicant may be released, yet the dressing will be maintained in its bubble configuration since it is locked in this position by the engagement of the hooks 16 with the adjacent layer No. 3. As discussed above, the remote ends of the hub and perimeter cylinders are fixedly anchored to the dressing layer No. 3 so as to enhance the stability of the dressing in its expanded configuration. As also noted above, layer No. 5 of the dressing, immediately above the expansion and support system described herein, is formed from the same type of criss-crossed material as layer No. 3. Therefore, the exposed hooks carried by the cylinder 14, when the dressing is transformed into its expanded configuration, may also engage the adjacent layer No. 5 to provided additional locking action and support for the dressing in its expanded configuration. Once the dressing has been transformed into its expanded configuration, the extended central bubble portion is positioned over the wound area, and the dressing is adhered to the skin of the patient at areas remote from the wound by the adhesive coated inner ends of layer No. 6.

As discussed above, the exposed springs housed within the flange 17 of the perimeter tube 10, after the springs have been released from the constraint of the cylinder 14, also serve to impede the retraction of the cylinder back into any of the tubes. Moreover, the cylinder 14 and the perimeter tube and hub tube may be provided with interlocking complimentary rims or flanges to act as stops for limiting the maximum distance of separation between the hub and perimeter tubes to prevent the cylinder from extending out completely beyond any one of the tubes. If this were to happen, the expanded bubble would have no structural support and would collapse. Preferably, the height of the expanded bubble should not exceed about 30% of the diameter of its base.

Figure 7A:
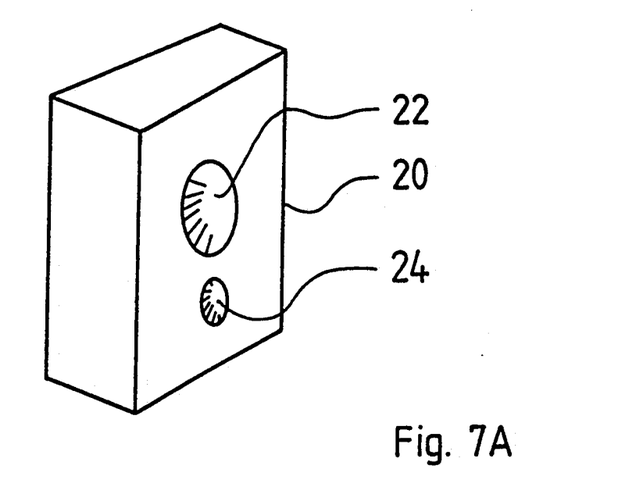
FIGS. 7A and 7B illustrate, respectively, a perspective and side elevational view of the package adapted to hold different size medical dressings in accordance with the present invention.
Figure 7B:
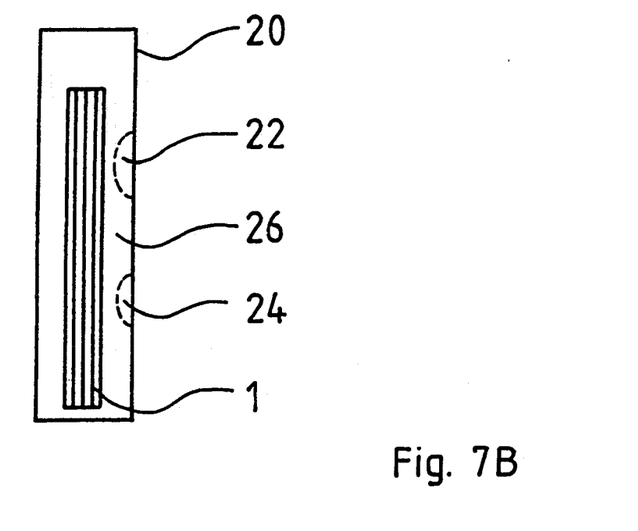

FIGS. 7A and 7B of the drawings illustrate a package for storing dressings in accordance with the present invention. As noted, dressings will be stored in a package 20 in the flat dressing configuration illustrated by FIG. 1 of the drawings. The package 20 defines two different sized recessed areas designated by reference Nos. 22 and 24. The dressing 1, in its flat storage configuration as illustrated by FIG. 1, is placed within the package 20 such that layer No. 1 is adjacent to the front surface of the package 20 defining recess areas 22 and 24. The package 20 is flexible so that a force may be exerted against the rear of the dressing by exerting a force against the rear surface 26 of the package 20. When such a force is exerted, the dressing is transformed into a bubble configuration as a result of the recessed areas 22, 24, or both, depending upon the area in which pressure is applied to the dressing. As a result of the support and locking system described above, the dressing is maintained in its expanded configuration after it is removed from the packaging to be applied to a wound area. Different packages 20 may be provided with different sized single recessed areas so that each dressing in the package may be expanded into a bubble configuration of the dimensions defined by the recessed area. Any package 20 may define one or more recessed areas of different dimensions so that the dressing housed therein may be expanded into a variety of different sized and dimensioned bubble configurations. Having now been pressed into its desired shape, the sterile packaging can be removed and the dressing applied to the skin in a manner in which the bubble is placed over the wound area.

Figure 5A:
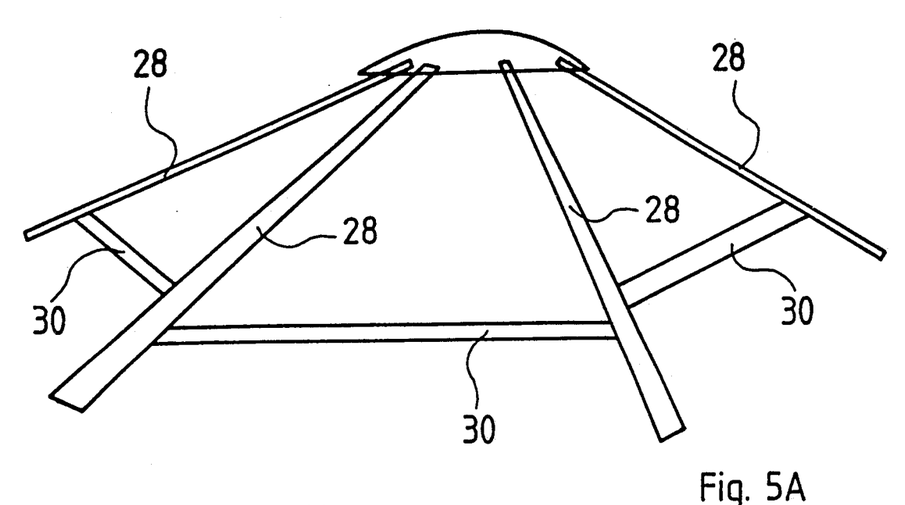
FIGS. 5A and 5B illustrate an alternative embodiment for the expansion and support system for the medical dressing shown both in expanded and non-expanded configuration.
Figures 5B, 5B:
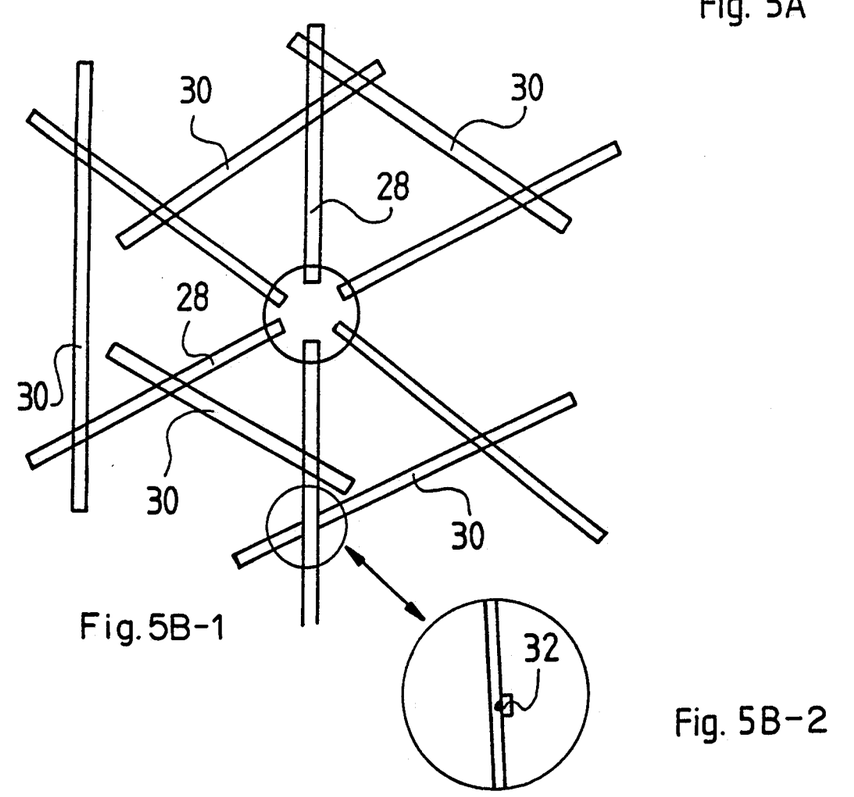

FIG. 5 of the drawings illustrates an alternative embodiment of the expansion and support means for the dressing of the present invention. Instead of employing a plurality of tubes with cylinders carrying hooks on their outer surfaces as described above, the expansion system of FIG. 5 provides a lattice arrangement of members 28 and 30. Members 28, which may be rods or tubes, are affixed at one end to a central or hub region of layer No. 3 of the dressing, while the other ends 28 are affixed to the peripheral regions of that layer. The members 28 are radially disposed in a spoke like configuration. Members 30, which are also affixed to layer No. 3 of the dressing, are oriented at an angle relative to the direction of extension of members 28. The members 30 carry a stop or stub 32 so that when the dressing is expanded, the stop 32 engages a surface of the members 8 to lock the dressing in the expanded configuration shown by FIG. 5A. It is of course possible to provide the stop on the members 28 instead of the members 30, or in the alternative, to provide other locking means between members 28 and 30, such as a complimentary tongue and groove arrangement.

Figure 6A:
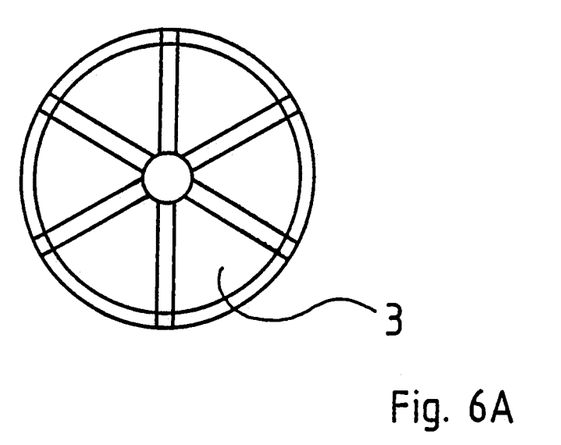
FIGS. 6A and 6B illustrate further alternative embodiments of the support and expansion system for the medical dressing of the present invention, shown both in non-expanded and expanded configurations.
Figure 6B:
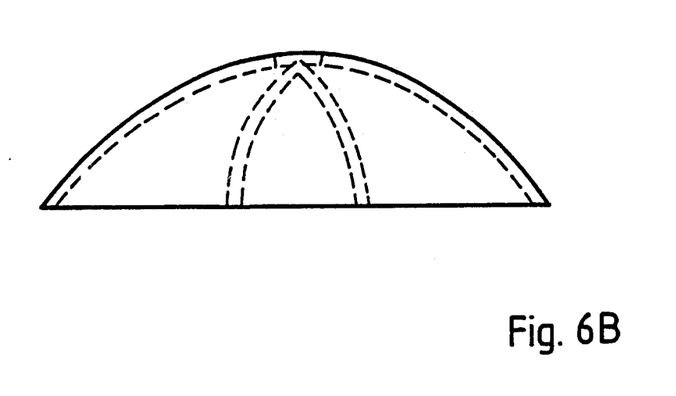

FIG. 6 of the drawings illustrates yet another alternative embodiment of the expandable medical dressing in accordance with the present invention. In this embodiment of the invention, layer No. 3 of the dressing defines a plurality of radially extended grooves, which extend from the center or hub portion of the layer to the periphery thereof. Strips of a flexible material, as for example a deformable plastic or wire, may be inserted into the grooves. When pressure is applied to the dressing, the strips of flexible material are deformed into the desired bubble configuration for the dressing. The elastic material from which the dressing is formed follows the configuration defined by the flexible strips.

It is also with the scope of the present invention to form the dressing from a single layer of material which is deformable and has "memory" to selectively maintain its deformed configuration. Preferably, the single deformable layer will be air permeable to permit both circulation and filtration of air into the wound area. The advantage of this embodiment of the invention is that the expanded configuration may be readily shaped into any three dimensional configuration as may best suit the needs of a patient. Moreover, an initial expanded configuration may be selectively transformed into a different configuration without replacing the first dressing.

In a further embodiment of the invention, the dressing may be permanently preformed in a specific expanded configuration. As in the other embodiments, the dressing preferably is formed from material which permits air flow into the wound area and filtration of the air entering the wound area. The preformed bubble preferably has a hard outer surface to protect the wound area.

It is further within the scope of the present invention to provide a dressing which is preformed, in part, and expansible, in part. For example, the dressing may comprise a preformed base or rim with a center portion which is expansible in the same manner as previously described herein. In the alternative, the center portion of the dressing may be preformed while the base is expansible in the manner described herein.

The different alternative embodiments of the expansion and support system for the dressing of the present invention may be used in combination with one another. For example, the embodiment illustrated by FIG. 5 which employs an expandable lattice system having stop means, may also be combined with the embodiment of FIGS. 2-4 which employs movable cylinders which expose hooks while locking the dressing in an expanded bubble configuration.

In all embodiments of the invention, the dressing is expanded into a bubble configuration for covering and protecting a wound area. Likewise, free circulation of air through the dressing and into the wound area is desireable to promote healing.

It is believed that other modifications and variations falling within the scope of the invention described herein will be apparent to those skilled in the art. The description of the invention is intended to be illustrative only, and not restrictive of the scope of the invention, that scope being defined by the following claims in all equivalence thereto.

I claim:

1. A dressing for protecting a wound area on a living being, said dressing comprising:
   at least a first layer for covering and protecting said wound area, and
   a second layer joined to said first layer, said second layer being oriented outwardly of said first layer relative to said wound area,
   said first and second layers including means for expanding said dressing to define an enclosed space between the joined first and second layers of said dressing and said wound area such that said dressing covers but does not directly contact said wound area.

2. The dressing of claim 1 wherein said first and second layers are formed from elastic material.

3. The dressing of claim 1 wherein said first and second layers are formed from porous material to permit circulation of air through said space defined by said dressing over said wound area.

4. The dressing of claim 3 wherein the pores of said material forming said first and second layers are sufficiently small to filter particles greater than a predetermined size from the air and prevent said particles from entering said space defined by said dressing over said wound area.

5. The dressing of claim 1 further including an outer layer disposed outwardly of said first and second layers relative to said wound area, said outer layer having at least the remote ends of an inner surface thereof coated with an adhesive material, said remote ends of said outer layer extending beyond the ends of said first and second layers for affixing said dressing to the skin of a living being away from said wound area.

6. The dressing of claim 1 wherein said means for expanding said dressing includes means for locking said dressing in an expanded configuration over said wound area.

7. The dressing of claim 6 wherein said means for locking includes at least one groove defined in said second layer, and at least one strip of deformable material received within said groove such that said first and second joined layers are selectively expandable over said wound area.

8. The dressing of claim 7 wherein said locking means includes a plurality of grooves defined in said second layer and radially oriented relative to each other, and at least one strip of deformable material received in each of said plurality of radially disposed grooves.

9. The dressing of claim 6 wherein said means for locking includes at least one supporting member having at least one hook mounted on its outer surface, said second layer comprising said at least one supporting member, and a third layer adjacent to said second layer adapted to engage said at least one hook carried by said at least one supporting member.

10. The dressing of claim 9 wherein said second layer comprises a plurality of said supporting members, each of said supporting members having at least one hook mounted on its outer surface, said plurality of supporting member being radially oriented relative to each other.

11. The dressing of claim 9 wherein said third layer is formed from a porous, elastic material.

12. The dressing of claim 9 wherein each of said supporting members having at least one hook mounted thereon is received within at least one tube for shielding said hook, said tube and said supporting member being movable relative to each other for selectively exposing said at least one hook mounted on said supporting member.

13. The dressing of claim 12 wherein each of said said supporting members having at least one hook mounted thereon is received within two adjacent tubes, said adjacent tubes being movable relative to each other for selectively exposing said at least one hook carried by each said supporting member received within said adjacent tubes.

14. The dressing of claim 13 including means for limiting the distance of separation between said adjacent tubes.

15. The dressing of claim 6 wherein said means for locking includes a plurality of supporting members having at least one hook mounted thereon arranged in a lattice configuration in said second layer, at least some of said supporting members have a stop for engaging other of said supporting members to secure said dressing in an expanded configuration over said wound area.

16. The dressing of claim 12 wherein a portion of said at least one tube for receiving said supporting member defines a widened chamber area for seating a resilient element, said resilient element being constrained in said widened chamber area by said supporting member when said supporting member engages said resilient element, said resilient element expanding to prevent retraction of said supporting member past said widened chamber area of said tube after said supporting member is disengaged from said resilient element.

17. A dressing for protecting a wound area on a living being, said dressing comprising at least one layer of deformable material which is selectively expandable over said wound area to define an enclosed space between said at least one layer and said wound area to avoid direct contact between the dressing and the wound area when said at least one layer is in its operative expanded configuration, said dressing being capable of being stored in a substantially flat configuration before being selectively expanded into an operative configuration.

18. The dressing of claim 17 wherein said at least one layer is formed from a porous material.

19. The dressing of claim 17 wherein said at least one layer is formed from an elastic material.

20. The dressing of claim 17 further including means for locking said dressing in said expanded configuration over said wound area.

21. The dressing of claim 17 further including a second layer joined to the outer surface of said first layer, said second layer being oriented outwardly of said first layer relative to said wound area, said second layer having remote ends extending beyond the ends of said first layer, said extended remote ends of said second layer being coated with an adhesive material for affixing said dressing to the skin of a living being away from said wound area.

22. The dressing of claim 17 further including a package for storing said dressing in a substantially flat configuration, said package including at least one recessed area having a predetermined shape for applying a force to said dressing for expanding said at least one layer of deformable material of said dressing into a configuration defined by said predetermined shape of said at least one recessed area.

23. The dressing of claim 22 wherein said package includes at least two differently dimensioned recessed areas such that said dressing may be selectively expandable into a configuration defined by either of said recessed areas by pressing said dressing thereagainst.

24. A dressing for protecting a wound area on a living being, said dressing comprising:
a preformed structure having a predetermined shape adapted to be applied to the skin of a living being to cover a wound area without directly contacting said wound area, said preformed structure defining an enclosed area over said wound area, said preformed structure being formed from porous material to permit circulation of air through said enclosed area defined over said wound area.

25. The dressing of claim 24 wherein said preformed structure defines an outer base of said dressing, said dressing further including an expansible inner area substantially centrally disposed within said outer base.

26. The dressing of claim 24 including an expansible outer base portion and an inner portion defined within said outer base portion, said inner portion of said base comprising said preformed structure.

27. The dressing of claim 24 wherein said dressing comprises said preformed structure configured to define said enclosed area over said wound area.

28. The dressing of claim 27 wherein the outer surface of said preformed structure is hardened to protect the wound area.

* * * * *